United States Patent [19]

Douwes

[11] Patent Number: 4,652,678
[45] Date of Patent: Mar. 24, 1987

[54] PROCESS FOR THE RECOVERY OF VALUABLE COMPONENTS FROM THE WASTE STREAMS OBTAINED IN THE PREPARATION OF UREA

[75] Inventor: Adolphe M. Douwes, Geleen, Netherlands

[73] Assignee: Stamicarbon B.V., Geleen, Netherlands

[21] Appl. No.: 659,307

[22] Filed: Oct. 10, 1984

Related U.S. Application Data

[63] Continuation of Ser. No. 377,138, May 11, 1982, abandoned.

[30] Foreign Application Priority Data

May 15, 1981 [NL] Netherlands .......................... 8102391

[51] Int. Cl.$^4$ ............................................. C07C 126/02
[52] U.S. Cl. ...................................... 564/73; 210/750; 423/237; 423/238; 423/358; 423/437; 564/67; 564/69
[58] Field of Search .............................. 564/69, 67, 73

[56] References Cited

U.S. PATENT DOCUMENTS

| 2,854,482 | 9/1958 | Guyer ..................................... 564/73 |
| 3,025,571 | 3/1962 | Beecher et al. .................... 564/73 X |
| 3,979,392 | 9/1976 | Eguchi et al. ..................... 564/73 X |
| 4,087,513 | 5/1978 | Schell ................................ 564/73 X |
| 4,138,434 | 2/1979 | Lagana et al. ........................ 564/69 |
| 4,341,640 | 7/1982 | Landis ............................... 564/73 X |

FOREIGN PATENT DOCUMENTS 1528051 10/1978 United Kingdom .

*Primary Examiner*—Robert V. Hines
*Attorney, Agent, or Firm*—Cushman, Darby & Cushman

[57] ABSTRACT

An improved process for recovering usable components from waste streams containing urea, including a dilute aqueous urea solution, which result from the preparation of particulate urea products. The dilute aqueous urea solution is used to wash a urea containing waste gas stream whereby urea contained in the gas stream is dissolved in the aqueous urea solution. The aqueous urea solution thus obtained is then subjected to a hydrolysis treatment whereby the urea contained therein is hydrolyzed, and the ammonia and carbon dioxide thus formed are separated from the residual liquid stream.

5 Claims, 1 Drawing Figure

PROCESS FOR THE RECOVERY OF VALUABLE COMPONENTS FROM THE WASTE STREAMS OBTAINED IN THE PREPARATION OF UREA

This is a continuation, of application Ser No. 377,138 filed May 11, 1982 and now abandoned.

BACKGROUND OF THE INVENTION

This invention relates to a process for the recovery of valuable components from the off-gases of a urea granulation system as well as from the liquid waste streams obtained in the preparation of urea.

In the preparation of urea from ammonia and carbon dioxide, a high temperature and correspondingly high pressure are used to form a urea synthesis solution which, in addition to product urea, still contains a considerable amount of free ammonia and unconverted ammonium carbamate. This urea synthesis solution is thereafter treated in one or more stages to decompose the ammonium carbamate into ammonia and carbon dioxide which are then mostly removed from the solution, together with the free ammonia present, and are usually recycled. From the last carbamate decomposition stage, an aqueous urea solution is obtained which still contains some dissolved ammonia and carbon dioxide, which are subsequently removed by expansion of the urea product stream to atmospheric or lower pressure. The resulting aqueous urea solution is then concentrated by evaporation and/or crystallization and further processed.

During this evaporation and crystallization, a gas mixture is formed which, in addition to water vapor, contains entrained fine urea droplets, as well as ammonia and carbon dioxide. This gas mixture is condensed, and the resulting condensate, together with the condensate formed from the gas mixture separated in the expansion of the urea solution after the last decomposition stage, becomes what is called process condensate. Part of this process condensate is returned into the process for the absorption of the gas mixture discharged from the last ammonium carbamate decomposition stage. The remaining portion of this process condensate is generally drained off or discharged from the process.

The process condensate also includes water initially introduced into the process as steam for the operation of the ejectors in the evaporation and/or crystallization section, wash water, rinsing water on the packing glands of the carbamate pumps and the like. Furthermore, for each mole of urea produced, one mole of water is formed. This means that, in a urea plant having a capacity of 1000 tons of urea per day, 300 tons of water will be formed in the synthesis. In addition, depending upon the temperature of cooling water used, approximately 200 to 315 tons per day of water are introduced into the process, so that in total roughly 500–615 tons of water may have to be discharged from the process per day.

This process condensate generally contains about 2 to 9 percent by weight ammonia, 0.8 to 6 percent by weight carbon dioxide, and 0.3 to 1.5 percent by weight urea. To simply discharge these materials from the process with the process condensate represents, on one hand, a loss of a substantial quantity of raw materials. On the other hand, this represents a substantial load to the surface waters into which this waste water would be discharged, and is no longer permitted in many countries.

If the urea product is intended for use as a fertilizer, then the further processing after the evaporation or crystallization step as a rule consists of granulation. A frequently used method of granulation is prilling, wherein a virtually anhydrous melt of urea is sprayed into a prilling tower in counterflow with a cooling gas, generally air. The virtually anhydrous melt can be obtained either by evaporation of aqueous urea solutions, or by melting urea crystals. Another known method for the preparation of urea granules is the spraying of highly concentrated urea solutions or urea melts onto fine urea particles or seeds maintained in a fluidized state by air.

In either of these techniques, large amounts of air are discharged from the granulation system, in which fine liquid and/or solid urea particles are suspended. In a urea plant having a capacity of 1000 tons of urea per day, this air contains approximately 30 to 40 kg urea dust per hour if the granulation by prilling, and can even be approximately 80 kg urea dust per hour when the fluid-bed granulation technique is applied. If this air were to be simply vented to the atmosphere, these amounts of urea dust would constitute a substantial loss of valuable product, and moreover would represent a degree of air pollution which is neither desirable nor permitted in many countries.

Methods are already known for removing the greater part of the ammonia and urea present in process condensate streams before such process condensate is discharged to the environment. One such method is described in Industrial Wastes, September/October, 1976, pages 44–47, wherein process condensate obtained in a urea synthesis plant, which has already been freed of a portion of this ammonia and carbon dioxide by desorption at a low pressure, is introduced into the bottom of a reaction column at a higher pressure wherein it is heated by means of steam resulting in the hydrolysis of urea. The solution thus obtained, containing ammonia and carbon dioxide, together with a small amount of non-hydrolyzed urea, is removed from the top of the reaction column, and expanded to the aforementioned low pressure whereupon the ammonia and carbon dioxide are removed in a second desorption column by stripping with steam. The gas mixture removed from the second desorption column can be used as a stripping medium in the first desorption stage.

The bottom product from the second desorption column is discharged to waste after it is used to heat a further portion of process condensate to be treated. Under practical conditions, however, this waste stream will still contain approximately 50 ppm ammonia and 50 ppm urea. Even after very long residence times, for which inefficiently large reaction columns would be required, it is not possible to achieve urea and ammonia contents in accordance with this method of less than 20 to 25 ppm.

In an improved process for the treatment of process condensate disclosed in copending application Ser. No. 325,922, filed Nov. 30, 1981, and now U.S. Pat. No. 4,456,535 the hydrolysis of the urea contained in the process condensate is carried out in counterflow with an inert gas, preferably steam, in a reaction column wherein the bottom temperature is maintained at about 180° to 230° C., and the top temperature is maintained at about 170° to 220° C. In this manner, the ammonia and urea contents of the residual waste liquid stream can be reduced to a level of 10 ppm or less.

However, neither the above-noted article nor patent application contain any suggestion of means to remove the pollutants from the air stream resulting from urea granulation.

One known method for treating air which is discharged from a urea granulation process is disclosed in British Pat. No. 1,528,051. In this process, the air discharged from the granulation process, containing entrained urea particles is introduced into the bottom of a washing column wherein it is passed countercurrently against a dilute aqueous urea solution which has been obtained by the condensation of vapors from the urea solution evaporation stage. In this manner, the urea particles entrained in the air stream are washed out and dissolved in the aqueous urea solution. The urea solution discharged from the bottom of the washing column is led back into the first evaporation stage. By reason of the heat exchange between the hot air from the granulation system and the wash liquid in the washing column, water is evaporated so that a mixture of air and water vapor is discharged and vented from the top of the washing column.

This known process has the disadvantage that any pollutants present in the urea used for the granulation are washed out in the washing column and end up in the urea solution to be evaporated. Moreover, any additives which may have been added to the urea melt prior to granulation, such as formaldehyde or formaldehyde derivatives, will also end up in the evaporation section via the wash liquid, and these additives can impede the evaporation process by the formation of foam. If it is desired that the urea solution recycled to the evaporation section is fairly concentrated, for instance 20 to 25 weight percent urea, then the wash liquid must be recirculated over the washing column which presents the danger of entrainment of droplets of fairly concentrated urea solution in the gas stream, resulting in a considerably greater loss of urea than when the washing solution need not be recirculated. Moreover, if glass fibers are used as a packing material in the washing column, there is a real danger of attack on this packing material resulting from the high pH of the solution due to the presence of ammonia and ammonium cyanate formed in the hydrolysis of urea.

SUMMARY OF THE INVENTION

It is an object of the present invention to provide a process whereby the useful and valuable components present in the off gases of a urea granulation system, as well as the components present in process condensate formed in the preparation of urea, can be recovered while avoiding the above-mentioned disadvantages of the known processes.

It has been found that the dilute aqueous urea solutions present in the waste liquid streams, such as process condensate produced during the preparation of urea, can advantageously be used to recover the urea contained in the waste gas stream from the granulation step. Specifically, it has been found that this dilute aqueous urea solution, prior to the hydrolysis treatment, can be first used to wash the waste gas stream thereby dissolving its urea content, and thereafter subjecting the resulting aqueous urea solution to the hydrolysis treatment. In this manner, the urea content of both the process condensate and the waste gas stream can be hydrolyzed together, and the resulting ammonia and carbon dioxide recovered, and reused, for instance, in the urea synthesis process.

When the dilute aqueous urea solution additionally contains ammonia, it is preferable to first remove substantially all of this ammonia prior to using the aqueous urea solution to wash the waste gas stream. Otherwise, desorption of some of the ammonia can occur during the washing step, and a portion of this valuable raw material will be lost. This ammonia can be removed from the urea solution by, for instance, subjecting the liquid waste stream to a stripping treatment using steam or some other inert gaseous stripping agent in a pre-desorption column maintained at a pressure of between about 1 and 5 bar.

It may be that only a portion of the waste liquid stream is required for the dissolution of the urea particles from the waste gas stream in the washing step. In this instance, it is economically advantageous to remove substantially all of the ammonia only from that portion of the dilute aqueous urea solution required for the washing step. However, in order to insure substantially complete hydrolysis of the urea in the hydrolysis column, it is desirable that the ammonia content of the aqueous urea solution fed thereto is at least partially reduced in its ammonia content.

Therefore, in a preferred embodiment where the waste liquid stream additionally contains ammonia, the removal of this ammonia can be carried out in two stages. In the first stage, sufficient ammonia is removed from that portion of the dilute aqueous solution not required for the washing step so that, when it is fed to the hydrolysis column, the hydrolysis of urea is not impeded, even in the lower zones of the column where the urea concentration is low. In the second stage, the ammonia is substantially completely removed from that portion of the dilute aqueous solution needed for dissolution of the urea particles in the waste gas washing step. The solution obtained in the first stage is thus fed to the hydrolysis treatment, and the solution obtained in the second stage of ammonia removal is used as the washing liquid and solvent for dissolution of the urea particles in the gaseous waste stream.

Preferably, the hydrolysis column is operated at a pressure of between about 10 and 45 bar. It has also been found of particular advantage to use as the heating and stripping agent in the hydrolysis column, steam at a pressure of between about 12 and 45 bar. The heat introduced by steam of this pressure is sufficient to hydrolyze the urea virtually completely in a relatively short time. Although inert gases other than steam can be applied, they must be separated out later, which involves extra cost.

The desorption of ammonia and carbon dioxide formed by the hydrolysis of urea can be carried out in a desorption column, preferably maintained at a pressure of between about 1 and 5 bar. The gas mixture obtained from this desorption column, as well as the gas mixture obtained from the top of the hydrolysis column after expansion to the pressure of the desorbed gas mixture, can advantageous be fed to the pre-desorption column as stripping and heating agents. Preferably, the desorption column and the pre-desorption column are operated at the same pressure.

The gases discharged from the pre-desorption column, comprised of a mixture of ammonia, carbon dioxide, and water vapor, can be fed, possibly after complete or partial condensation, to the low-pressure portion of the urea synthesis process for use in the synthesis of additional urea.

A further advantage of this process is that a portion of the water contained in the dilute aqueous urea solution used for washing the off-gases from the granulation system will be evaporated, thus reducing the load on the hydrolysis column. Depending on the quantity and temperature of this waste gas stream from the granulation system, 20 to 30 percent of the water contained in the process condensate stream can be evaporated. As a result, the load of the hydrolysis column is reduced by 20 to 30 percent, and the amount of high-pressure steam needed in the hydrolysis column, and also the amount of low-pressure steam needed in the desorption column, can be decreased. This advantage amply outweighs any disadvantage occasioned by the need for additional low-pressure steam for the complete removal of ammonia from at least a portion of the dilute aqueous urea solution used for the washing step.

In a typical urea installation, it has been found that the amount of additional urea to be hydrolyzed by reason of the washing of the gaseous waste stream is only slightly larger, at most 10 percent or more, than the amount that is already present in the waste liquid stream hydrolyzed in accordance with the known process.

DETAILED DESCRIPTION OF THE DRAWING

Figure 1:
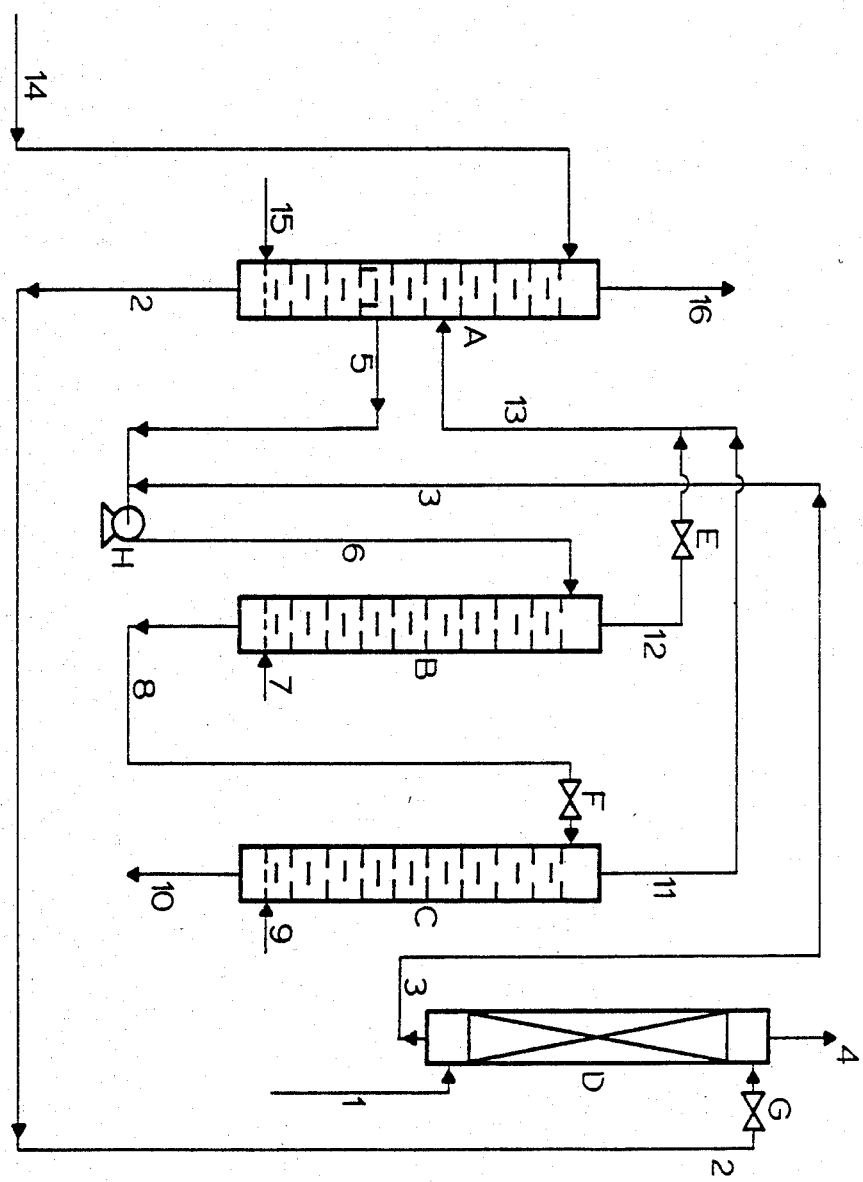

The attached drawing schematically illustrates one embodiment of the invention wherein process condensate derived from the urea synthesis process is used to recover the urea contained in the off-gases from the urea granulation system.

In this drawing, process unit A represents the pre-desorption column, unit B the hydrolysis column, and unit C the desorption column. Unit D is the washing column for washing out and dissolving the urea particles contained in the off-gases from the granulation system. The letters E, F, and G refer to expansion valves, while H represents a pump.

In pre-desorption column A, the process condensate supplied through line 14 is contacted, at a pressure of for instance 1 to 5 bar, with a gaseous mixture of water vapor, ammonia, and carbon dioxide supplied through line 13. Through line 5, a portion of the process condensate, partially freed of ammonia and carbon dioxide, is led to hydrolysis column B which operates at a pressure of, for instance, 10 to 42 bar. Through line 15, low pressure steam is fed to the bottom of pre-desorption column A, causing the desorption of ammonia still present in the condensate.

From the bottom of column A, a substantially ammonia-free aqueous urea solution is discharged through line 2, and is led into washing column D via expansion valve G. A urea dustladened off-gas from the urea granulation or prilling section is supplied to this column through line 1. The substantially urea-free off-gas, and water vapor resulting from evaporation of a portion of the washing solution, are discharged from washing column D through line 4.

The aqueous urea solution formed in the washing column, additionally containing the urea particles and any ammonia washed out of the gas stream, is discharged from washing column D through line 3 and pumped via pump H through line 6 into hydrolysis column B, together with a portion of the process condensate fed directly from pre-desorption column A through line 5. High-pressure steam is supplied to hydrolysis column B through line 7. The urea present in the aqueous urea solutions fed to this column is decomposed virtually quantitatively into ammonia and carbon dioxide. The steam introduced into this column provides not only the required amount of heat, but also serves as a stripping agent for driving off a portion of the ammonia and carbon dioxide formed by the hydrolysis.

The solution discharged from hydrolysis column B through line 8 is expanded to a pressure of from 1 to 5 bar through expansion valve F and is led into desorption column C. In this desorption column, low-pressure steam is fed through line 9 in order to remove the ammonia and carbon dioxide still remaining in the solution. The gas mixture discharged from the top of desorption column C through line 11 is fed into pre-desorption column A through line 13, together with the gas mixture discharged from hydrolysis or reaction column B, after this latter gas mixture has been expanded to the pressure of the former gas mixture in expansion valve E. A gas mixture is discharged from pre-desorption column A through line 16, which contains virtually the total amount of valuable components present in both the off-gas from the granulation system, as well as in the process condensate, in the form of ammonia and carbon dioxide.

DETAILED DESCRIPTION OF A PREFERRED EMBODIMENT

Using the process configuration as illustrated in the drawing and described above, process condensate, and air discharged from a prilling tower, obtained from a urea plant having an output of 1000 tons of urea per day, were treated. All quantities are given in kg/hr.

Process condensate, containing 5.0 wt. % $NH_3$, 3.15 wt. % $CO_2$, and 1.43 wt. % urea, was fed in an amount of 25,600 kg into pre-desorption column A at a pressure of 4 bar. This process condensate was passed countercurrently against 5100 kg of a gaseous mixture obtained from reaction column B and desorption column C, consisting of 243 kg $NH_3$, 293 kg $CO_2$, and 4564 kg water vapor, and had a temperature of 138° C. Steam, having a pressure of 4.5 bar and a temperature of 143° C. was fed into the bottom of the desorption column in a quantity of 2800 kg. Through line 2, 15,000 kg of a solution containing 188 kg urea, 5 kg $NH_3$, 1 kg $CO_2$, and 14,806 kg water was fed to the top of washing column D. Air from the prilling tower was fed into the bottom of washing column D, in an amount of 469,300 kg. This prilling tower air included 35 kg $NH_3$, 35 kg urea, and 100 kg water vapor, and had a temperature of 80° C. Together with the air discharged from the top of washing column D, 5 kg urea, 35 kg $NH_3$, and 8500 water vapor were discharged from the system. The solution obtained from the bottom of washing column D through line 3 contained 218 kg urea, 5 kg $NH_3$, 1 kg $CO_2$, and 6406 kg water. The solution obtained from pre-desorption column A through line 5 contained 177 kg urea, 15 kg $NH_3$, 3 kg $CO_2$, and 13,985 kg water. The respective solutions from the pre-desorption column and washing column were combined and pumped to a pressure of 37 bar by pump H and led into hydrolysis column B. Hydrolysis column B was also fed near the bottom thereof with 1000 kg steam having a temperature of 352° C. and a pressure of 38 bar. The space velocity within hydrolysis column B was controlled in such manner that the residence time of the liquid in the column was about 5 to 10 minutes. Virtually all of the urea present in the feed to the hydrolysis column was hydrolyzed into $NH_3$, and $CO_2$.

From the bottom of hydrolysis column B, 21,310 kg of a solution containing 203 kg $NH_3$, 20 kg $CO_2$, and 21,087 kg water was discharged through line 8. This solution was decreased in pressure to 4 bar through expansion valve F, and was thereafter treated in desorption column C with 4200 kg of steam having a pressure of 4.5 bar and a temperature of 143° C. From the bottom of desorption column C, 20,190 kg water containing less than 10 ppm urea and less than 10 ppm $NH_3$ was removed from the system. From the top of desorption column C, 4600 kg of a gas mixture composed of 203 kg $NH_3$, 20 kg $CO_2$, and 4377 kg of water vapor, and having a temperature of 136° C., was discharged through line 11.

From the top of hydrolysis column B, 500 kg of a gas mixture consisting of 40 kg $NH_3$, 273 kg $CO_2$, and 187 kg water vapor, having a temperature of 210° C., was discharged through line 12. After the pressure of this gas mixture discharged through line 12 had been lowered to 4.5 bar through expansion valve E, the mixture was led through line 13 into pre-desorption column A, together with the gas mixture supplied through line 11. From the top of pre-desorption column A, a gas mixture consisting of 1503 kg $NH_3$, 1089 kg $CO_2$, and 1728 water vapor was obtained. This latter gas mixture was subsequently led to the low-pressure part of the urea synthesis process for reuse in producing a further portion of urea.

In carrying out the process as described above in accordance with the invention, approximately 7000 kg of low-pressure steam and 1000 kg of high-pressure steam are needed per hour, and the heat content of the off-gases from the prilling tower result in the evaporation of approximately 8400 kg water.

On the other hand, if the process condensate and the off-gases from the prilling tower were treated separately, 6800 kg low-pressure steam and 1200 kg high-pressure steam would be needed for the decomposition of urea and desorption of the resulting $NH_3$ and $CO_2$, while the evaporation of the dilute aqueous solution obtained upon separation of the urea from the prilling tower off-gases would require an additional 200 kg low-pressure steam.

What is claimed is:

1. An improved process for the recovery of usable components from waste streams containing urea, including a dilute aqueous urea solution, which result from the preparation of particulate urea products and wherein said dilute aqueous urea solution is subjected to a hydrolysis treatment whereby at least a portion of said urea contained therein is hydrolyzed and the ammonia and carbon dioxide thus formed are separated from a residual liquid stream, the improvement comprising:
   passing said dilute aqueous urea solution, prior to said hydrolysis, in direct contact with a waste gas stream from a granulation system utilized to form said particulate urea products, whereby
   liquid or solid particles of urea suspended in said waste gas stream are washed therefrom and dissolved into said aqueous urea solution and
   a portion of the water contained in said dilute aqueous urea solution is vaporized into said waste gas stream, thereby increasing the concentration of said dilute aqueous urea solution with respect to urea, and
   thereafter subjecting said concentrated dilute aqueous urea solution to a hydrolysis treatment whereby at least a portion of the urea contained therein is hydrolyzed and the ammonia and carbon dioxide thus formed are separated and recovered from the residual liquid stream.

2. The process of claim 1 whrein said dilute aqueous urea solution additionally contains ammonia, and substantially all of said ammonia is first removed from said dilute aqueous urea solution prior to passing said solution in direct contact with said waste gas stream.

3. The process of claim 2 wherein ammonia is removed from said dilute aqueous urea solution in at least two stages, and wherein an aqueous urea solution having a reduced ammonia content obtained in a first said stage is subjected to said hydrolysis treatment without first being used to wash said waste gas stream, and an aqueous urea solution substantially free of ammonia obtained in a second said stage is used to wash said urea containing waste gas stream.

4. The process of claim 1 wherein said granulation system includes a prilling step.

5. The process of claim 1 wherein said granulation system includes a fluid-bed granulation step.

* * * * *